(12) United States Patent
Freund et al.

(10) Patent No.: US 6,262,307 B1
(45) Date of Patent: *Jul. 17, 2001

(54) SHAPED, ACTIVATED METAL, FIXED-BED CATALYST

(75) Inventors: Andreas Freund, Kleinostheim; Monika Berweiler, Maintal; Barbara Bender, Rodenbach; Bernd Kempf, Kleinwallstadt, all of (DE)

(73) Assignee: Degussa-Huls Aktiengesellschaft, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/080,466

(22) Filed: May 19, 1998

(30) Foreign Application Priority Data

May 26, 1997 (DE) ................................. 197 21 898

(51) Int. Cl.[7] ........................... C07C 209/00; B01J 23/40
(52) U.S. Cl. ........................ 564/416; 502/326; 564/495; 568/891
(58) Field of Search ............................ 502/326; 564/416, 564/495; 568/891

(56) References Cited

U.S. PATENT DOCUMENTS

| | | |
|---|---|---|
| 3,337,334 | 8/1967 | Fenn et al. . |
| 3,340,551 | 4/1966 | Hopkins . |
| 3,351,495 | 11/1967 | Wayne et al. . |
| 4,153,578 | 5/1979 | De Thomas et al. . |
| 4,826,799 | 5/1989 | Cheng et al. . |

FOREIGN PATENT DOCUMENTS

| | | |
|---|---|---|
| 2159736 | 6/1973 | (DE) . |
| 4446907A1 | 7/1996 | (DE) . |
| 0437788B1 | 7/1991 | (EP) . |
| 0648534A1 | 9/1994 | (EP) . |

OTHER PUBLICATIONS

Jun. 1993, DIN 66133, Degussa "Bestimmung der Porenvolumenverteilung, und der spezifischen Oberfläche von Feststoffen durch Quecksilberintrusion", pp. 1–3.

Feb. 1998, DIN 66134, Degussa Bestimmung der Porengrössenverteilungund der spezifischen Oberfläche mesoporöser Feststoffe durch Stickstoffsorption, pp. 1–7.

*Primary Examiner*—Paul J. Killos
(74) *Attorney, Agent, or Firm*—Smith, Gambrell & Russell, LLP

(57) ABSTRACT

A shaped, activated metal, fixed-bed catalyst with a pore volume of 0.05 to 1 ml/g and an outer activated layer consisting of a sintered, finely-divided, catalyst alloy and optionally promoters. The catalyst alloy has metallurgical phase domains, resulting from the method of preparation of the alloy, in which the largest phase by volume has a specific interface density of more than 0.5 $\mu m^{-1}$.

20 Claims, No Drawings

SHAPED, ACTIVATED METAL, FIXED-BED CATALYST

INTRODUCTION AND BACKGROUND

The present invention relates to a shaped, Raney metal, fixed-bed catalyst activated in an outer layer.

Activated metal catalysts are known in the field of chemical engineering as Raney catalysts. They are used, largely in powder form, for a large number of hydrogenation, dehydrogenation, isomerization and hydration reactions of organic compounds. These powdered catalysts are prepared from an alloy of a catalytically-active metal, also referred to herein as a catalyst metal, with a further alloying component which is soluble in alkalis. Mainly nickel, cobalt, copper or iron are used as catalyst metals. Aluminum is generally used as the alloying component which is soluble in alkalis, but other components may also be used, in particular zinc and silicon or mixtures of these with aluminum.

These so-called Raney alloys are generally prepared by the ingot casting process. In that process a mixture of the catalyst metal and, for example, aluminum are first melted and then cast into ingots. Typical alloy batches on a production scale amount to about 10 to 100 kg per ingot. According to DE-OS 21 59 736 cooling times of up to two hours are obtained. This corresponds to an average rate of cooling of about 0.2 K/s. In contrast to this, rates of cooling of $10^2$ to $10^6$ K/s are achieved in processes where rapid cooling is applied (for example an atomizing process). The rate of cooling is affected in particular by the particle size and the cooling medium (see Materials Science and Technology, Edited by R. W. Chan, P. Haasen, E. J. Kramer, Vol 15, Processing of Metals and Alloys, 1991, VCH-Verlag Weinheim, pages 57 to 110). A process of this type is used in EP 0 437 788 B1 in order to prepare a Raney alloy powder. In that process the molten alloy at a temperature of 50 to 50° C. above its melting point is atomized and cooled using water and/or a gas.

To prepare a catalyst, the Raney alloy is first finely milled if it has not been produced in the desired powdered form during preparation. Then the aluminum is entirely or partly removed by extraction with alkalis such as, for example, caustic soda solution. This activates the alloy powder. Following extraction of the aluminum the alloy powder has a high specific surface area (BET), between 20 and 100 $m^2/g$, and is rich in adsorbed hydrogen. The activated catalyst powder is pyrophoric and is stored under water or organic solvents or is embedded in organic compounds which are solid at room temperature.

Powdered catalysts have the disadvantage that they can be used only in a batch process and, after the catalytic reaction, have to be separated from the reaction medium by costly sedimentation and/or filtration. Therefore a variety of processes for preparing moulded items which lead to activated metal fixed-bed catalysts after extraction of the aluminum have been disclosed. Thus, for example, coarse particulate Raney alloys, i.e. Raney alloys which have been only coarsely milled, are obtainable and these can be activated by treatment with caustic soda solution. Extraction and activation then occurs only in a surface layer the thickness of which can be adjusted by the conditions used during extraction.

A substantial disadvantage of catalysts prepared by these prior methods are the poor mechanical stability of the activated outer layer. Since only this outer layer of the catalyst is catalytically active, abrasion leads to rapid deactivation and renewed activation of deeper lying layers of alloy using caustic soda solution then leads at best to partial reactivation.

Patent application EP 0 648 534 A1 describes shaped, activated Raney metal fixed-bed catalysts and their preparation. These avoid the disadvantages described above, such as e.g. the poor mechanical stability resulting from activating an outer layer. To prepare these catalysts, a mixture of powders of a catalyst alloy and a binder are used, wherein the catalyst alloys each contain at least one catalytically active catalyst metal and an extractable alloying component. The pure catalyst metals or mixtures thereof which do not contain extractable components are used as binder. The use of the binder in an amount of 0.5 to 20 wt. %, with respect to the catalyst alloy, is essential in order to achieve sufficient mechanical stability after activation. After shaping the catalyst alloy and the binder with conventional shaping aids and pore producers, the freshly prepared items which are obtained are calcined at temperatures below 850° C. As a result of sintering processes in the finely divided binder, this produces solid compounds between the individual granules of the catalyst alloy. These compounds, in contrast to the catalyst alloys, are non-extractable or only extractable to a small extent so that a mechanically stable structure is obtained even after activation. However, the added binder has the disadvantage that it is substantially catalytically inactive and thus the number of active centers in the activated layer is reduced. In addition, the absolutely essential use of a binder means that only a restricted range of amounts of pore producers can be used without endangering the strength of the shaped item. For this reason, the bulk density of these catalysts cannot be reduced to a value of less than 1.9 kg/l without incurring loss of strength. This leads to a considerable economic disadvantage when using these catalysts in industrial processes. In particular when using more expensive catalyst alloys, for example cobalt alloys, the high bulk density leads to a high investment per reactor bed, which is, however, partly compensated for by the high activity and long term stability of these catalysts. In certain cases, the high bulk density of the catalyst also requires a mechanically reinforced reactor structure.

An object of the present invention is therefore to provide a shaped, activated metal, fixed-bed catalyst which largely avoids the disadvantages of known fixed-bed catalysts referred to above.

SUMMARY OF THE INVENTION

The above and other objects of the invention are achieved by a shaped, activated metal, fixed-bed catalyst with a pore volume of 0.05 to 1 ml/g with an outer activated layer consisting of a sintered, finely-divided, catalyst alloy and optionally promoters, wherein the catalyst alloy has metallurgical phase domains, resulting from the method of preparation of the alloy, in which the phase with the greatest volume has a specific interface density of more than 0.5 $\mu m^{-1}$.

The specific interface density $S_v$ is a metallographic parameter which describes the fineness of the phase structure of an alloy and is defined by the following equation:

$$S_v = \frac{4}{\pi} \cdot \frac{\text{Perimeter (phase)}}{\text{Area (phase)}} [\mu m^{-1}]$$

This parameter is introduced, for example, in U.S. Pat. No. 3,337,334 as the "complexity index" C.I. The specific interface density $S_v$ defined here differs from the complexity index cited in U.S. Pat. No. 3,337,334 only by the proportionality constant $4/\pi$. The larger $S_v$, the smaller the corresponding phase domains. The entire disclosure of U.S. Pat.

No. 3,337,334 is relied on and incorporated herein by reference for this purpose.

An essential feature of the catalyst according to the invention is a phase structure incorporating the smallest possible volumes. This type of phase structure is obtained when the phase occupying the greatest volume in the alloy has a specific interface density of more than 0.5 $\mu m^{-1}$.

DETAILED DESCRIPTION OF INVENTION

The present invention will now be described in further detail.

The specific interface density can be determined by a quantitative metallographic test in accordance with U.S. Pat. No. 3,337,334. For this purpose, a transverse section is prepared from a granule of the catalyst alloy and examined under a microscope. The different phases in the catalyst alloy appear in different shades of grey under an optical microscope in the polished, in particular in a contrasted or etched, state. Using the different grey values, the structure can be evaluated using an automatic, PC-supported, image analysis system. The phases which are present can be identified by analyzing the composition using energy-dispersive X-ray analysis. For example, the phases $Al_3Ni_2$, $Al_3Ni$ and an $Al$—$Al_3i$ eutectic have been observed in a Ni/Al alloy with the composition of about 50 wt. % nickel and 50 wt. % aluminum, in accordance with the phase diagram (see ASM Specialty Handbook® "Aluminum and Aluminum Alloys", edited by J. R. Davis, 3rd edition, page 522, 1994).

To characterize the catalyst alloy, the phase occupying the greatest volume of the alloy is first determined. The specific interface density of this phase is then determined in an appropriate manner using modern image analysis processes.

Surprisingly, it was found that when using catalyst alloys with a phase structure incorporating small volumes, in which the largest phase by volume has a specific interface density of more than 0.5 $\mu m^{-1}$, catalysts according to the invention can be prepared without adding a binder. A mechanically stable structure with a high abrasion resistance is produced, despite the lack of a binder. When preparing the catalyst, pore producers can be added in larger amounts than in catalysts known from the prior art, due to the lack of a binder. This facilitates the preparation of catalyst materials with a larger pore volume. The lack of a largely inert binder and the high pore volume lead to catalysts with high volume-specific activity.

Raney catalyst alloys are typically obtained from a melt of the catalyst metal and aluminum. Nevertheless, different phase structures may be obtained from identical macroscopic compositions, depending on how and how fast the molten material is cooled. A coarse phase structure with large phase domains is generally produced when casting ingots, due lo the low rate of cooling. A substantially finer structure is produced, however, when a more rapid cooling procedure is used. The rate of cooling required can be determined by a person skilled in the art by appropriate trials. Only small batches of alloy can be processed in an ingot casting process. As a guideline for the rates of cooling required, cooling times from the melting point down to less than 700° C. of less than two minutes may be mentioned. This corresponds to rates of cooling of at least 5 K/s. Rates of cooling of more than 10, in particular of more than 50 K/s, are preferably used. The powder preparation process in accordance with EP 0 437 788 B1 generally provides alloy powders with a suitable phase structure. The entire disclosure of EP 0 437 788B1 is relied on and incorporated herein for that purpose.

Alloy powders with average particle sizes of 10 $\mu m$ to 1000 $\mu m$ may be used for preparing catalysts according to the invention. However, the bulk density of the alloy powder is also important for highly active catalysts. This should be in a range from 1.0 to 3.0 kg/l. If the bulk density is more than 3.0 kg/l the catalysts are too compact and thus less active. Bulk densities of less than 1.0 kg/l lead to defective mechanical stability in the catalyst materials. A particularly high volume activity for the catalysts can be produced if the alloy powder has an average particle size of more than 100 $\mu m$ and a bulk density of less than 1.6 kg/l.

The ratio by weight of catalyst metal to extractable alloying component in the catalyst alloy is, as is conventional with Raney alloys, in the range from 20:80 to 80:20. Catalysts according to the invention may also be doped with other metals in order to have an effect on the catalytic properties. The purpose of this type of doping is, for example, to improve the selectivity in a specific reaction. Doping metals are frequently also called promoters. The doping or promoting of Raney catalysts is described for example in U.S. Pat. No. 4,153,578, in DE-AS 21 01 856, in DE-OS 21 00 373 and in DE-AS 20 53 799.

In principle, any known metal alloys with extractable elements such as aluminum, zinc and silicon may be used for the present invention. Suitable promoters are the transition metals in groups 3B to 7B and 8 and group 1B of the Periodic Table of Elements and also the rare-earth metals. They are used in an amount of up to 20 wt. %, with respect to the total weight of catalyst. Chromium, manganese, iron, cobalt, vanadium, tantalum, titanium tungsten and/or molybdenum and metals from the platinum group are preferably used as promoters. They are expediently added as alloying constituents in the catalyst alloy. In addition, promoters with a different extractable metal alloy, in the form of a separate metal powder, may be used or the promoters may be applied later to the catalyst material. Later application of promoters may be performed either after calcination or after activation. Optimum adjustment of the catalytic properties to the particular catalytic process is thus possible.

The catalyst alloy and optionally promoters in the form of powders are processed to give a shapeable material by adding moistening agents and/or additives such as shaping aids, lubricants, plasticizers and optionally pore producers. Any conventional materials used for this purpose may be used as lubricant, plasticizer or pore producer. A number of suitable materials is mentioned in U.S. Pat. Nos. 4,826,799, 3,404,551 and U.S. Pat. No. 3,351,495 which are relied on and incorporated herein by reference. Waxes, such as for example, Wax C micropowder PM from Hoechst AG, fats such as magnesium or aluminum stearate or carbohydrate-containing polymers such as tylose (methyl cellulose) are preferably used. The solids in the mixture are carefully homogenized in suitable mixers or kneaders, if necessary with the addition of a moistening agent. Suitable moistening agents are water, alcohols, glycols, polyether glycols or mixtures thereof. The purpose of homogenization is to prepare the mixture for the subsequent shaping process. Extrusion, pelleting or compacting may be applied. The type and sequence of introduction of additives depends on the shaping process to be used. Thus, extrusion requires a plastic material with a specific viscosity, whereas a free-flowing material which is easy to meter out is required for pelleting. The techniques to be applied for these purposes such as, for example, agglomeration to produce a free-flowing powder or adjustment to the correct viscosity for extrusion are used as a matter of routine by a person skilled in the art.

The shaped items may be produced in any shape conventionally used in catalyst engineering. Depending on the requirements of the particular application, extrudates, spheres, rings, spoked rings or pellets may be prepared. The final shaped items are, if required, dried to constant weight at temperatures between 80 and 120° C. and then calcined at temperatures below 850° C., preferably between 200 and 700° C., in air in continuous or batch-operated furnaces such as rotary tube furnaces, conveyor belt calciners or static furnaces. The organic additives are then burnt away and a corresponding pore system is produced.

The pore structure and pore volume of the catalysts can be varied by means of appropriate selection of the type and amount of pore-producing additive. The final pore structure and pore volume which is produced are also affected by the average particle size of the catalyst alloy powder used and the type of compacting applied. By appropriate selection of the parameters mentioned, the structure of the moulded item can be adjusted to the requirements of the particular catalytic process.

During calcination of the shaped items, the particles in the alloy powder sinter together and provide the shaped items with high mechanical stability and good resistance to abrasion. Typically, the values for the hardness of cylindrical pellets after calcination are between 50 and 400 N (measured radially in accordance with ASTM D 4179-82). As a result of the high specific interface density and the increased reactivity for solid reactions which is produced, a stable, porous structure is produced under the calcination conditions selected. When comparing the phase structure before and after calcination, it can be seen that the desired solid reaction is associated with only a negligible reduction in the specific interface density. The specific interface density, however, is still above 0.5 $\mu m^{-1}$ even in the final shaped items constituting the catalyst.

The catalyst precursors resulting from calcination are also very important with regard to the economic viability of the invention. They are not pyrophoric and can therefore be handled and transported without difficulty. Activation can be performed by the user shortly before use. Storage under water or organic solvents or embedding in organic compounds is not required for the catalyst precursors.

As compared with the final catalysts, the catalyst precursors are items with a homogeneous composition consisting of an intimate mixture of particles of the catalyst alloy and optionally one or more promoters which are sintered to give a mechanically stable and porous shaped item. The densities, depending on the composition of the catalyst alloy and on the pore volume, as from 1.0 to 2.5 kg/l. Pore volumes range from 0.5 to 1 ml/g and are advantageous. Since the catalyst precursors have not been activated, their specific surface area is less than 20, generally less than 10 m²/g.

More than 99% of the catalyst precursor consists of the catalyst alloy and the optionally-contained promoters. During calcination of the precursors at temperatures of less than 850° C., a very small proportion of surface oxides is produced, but these are removed during activation with an alkali and therefore have no effect on the subsequent catalytic properties.

After calcination, the shaped items are activated by extraction of the aluminum using caustic soda solution. For this purpose, for example, a 20% strength caustic soda solution heated to 80° C. may be used. A treatment time of two hours, depending on the porosity of the calcined shaped item, leads to an active outer layer with a thickness of about 0.1 to 1.0 mm. It has been demonstrated in particular that the hardness of shaped items which have been compacted at low pressure is increased greatly by the extraction procedure.

The examples which follow are used to explain the invention in more detail. Although only a few preferred embodiments of the invention are presented in the examples, the present invention enables a person skilled in the art to prepare activated Raney metal fixed-bed catalysts with a wide range of parameters which he can adapt to the particular requirements of the application.

As a measure of the amount of catalytically active centers in the catalysts, their oxygen absorption was determined using temperature programmed oxidation (TPO). In the case of nickel catalysts, for example, each activated nickel atom can take up one oxygen atom as a result of oxidation.

To perform TPO, about 5 to 10 g of the water-moist, activated catalyst material was dried in a U-shaped quartz glass tube (internal diameter: 1 cm, length of one arm: 15 cm) in a stream of nitrogen flowing at 10 l/h, at 120° C., for a period of 17 hours. The furnace was then carefully cooled to −190° C. using liquid nitrogen. After reaching a constant reactor temperature, the pure nitrogen flow was cut off and nitrogen containing 4 vol. % of oxygen was passed over the sample at a rate of 10 l/h. Analysis of the oxygen content of the sample was performed using an "Oxynos 100" from the Leybold-Heraeus company, which depends on a paramagnetic principle of measurement. After reaching a constant oxygen content at about −120° C., a temperature gradient of 6° C./min was applied. The shape of the oxygen absorption curve was determined over the temperature range from −100° C. to +550° C. The amount of oxygen absorbed was determined from the area under the oxygen absorption curve. The amount of absorbed oxygen is quoted in mmol $O_2$/g of catalyst.

The metal alloys A to E listed in table 1 were used to prepare catalysts according to the invention. These alloy powders were cooled particularly rapidly during their preparation from a molten material and therefore had a phase structure incorporating very small volumes. The alloy powder CC used to prepare a comparison catalyst was a material which is regularly used to produce activated metal powder catalysts and metal fixed-bed catalysts.

Determining the specific interface density $S_v$ is a costly procedure and was therefore only determined for alloy powders CC and A and a reference sample. The interface densities of alloy powders B to E were determined qualitatively by comparison with the reference sample. To produce the reference sample, 100 g of coarse fragments of NiAl alloy CC (table 1) were melted and 4 rods were cast with a diameter of 7 mm and a length of 15 cm. A high rate of cooling could be achieved due to the large surface area of the rods. The cooling time of these rods from the melting point to below 700° C. was about one minute.

Using the quantitative metallographic method described above, it was shown that the $Ni_2Al_3$ phase in this reference sample had a volume fraction of 67.4% and a specific interface density of 0.5 $\mu m^{-1}$. To estimate the specific interface densities of alloys B to E, optical microscope photographs of transverse sections were taken at 200× and 500× magnification and compared with the corresponding photographs of the reference sample.

TABLE 1

Alloy powders

| Alloy | Parameters | Data |
|---|---|---|
| CC | Ni/Al ratio | 53/57 |
|  | $S_v$ ($Ni_2Al_3$ 65.7 vol. %) ($\mu m^{-1}$) | 0.08 |
|  | Volume-specific, average particle diameter ($\mu m$) | 50 |
|  | Bulk density (kg/l) | 2.23 |
| A | Ni/Al ratio | 50/50 |
|  | $S_v$ ($Ni_2Al_3$ 57.1 vol. %) ($\mu m^{-1}$) | 1.6 |
|  | Volume-specific, average particle diameter ($\mu m$) | 124 |
|  | Bulk density (kg/l) | 1.40 |
| B | Ni/Al ratio | 50/50 |
|  | $S_v$ ($\mu m^{-1}$) | >0.5 |
|  | Granular fraction ($\mu m$) | 500–1400 |
|  | Bulk density (kg/l) | 1.6 |
| C | Ni/Cr/Al ratio | 50/1.5/48.5 |
|  | $S_v$ ($\mu m^{-1}$) | >0.5 |
|  | Volume-specific, average particle diameter ($\mu m$) | 32 |
|  | Bulk density (kg/l) | 1.47 |
| D | Cu/Al ratio | 50/50 |
|  | $S_v$ ($\mu m^{-1}$) | >0.5 |
|  | Volume-specific, average particle diameter ($\mu m$) | 48 |
|  | Bulk density (kg/l) | 1.48 |
| E | Cu/Zn/Al ratio | 50/15/35 |
|  | $S_v$ ($\mu m^{-1}$) | >0.5 |
|  | Volume-specific, average particle diameter ($\mu m$) | 50 |
|  | Bulk density (kg/l) | 1.75 |

COMPARISON EXAMPLE 1

A very free-flowing, pelletable catalyst mixture was prepared in accordance with the instructions in EP 0 648 534 A1 for a comparison catalyst consisting of 1000 g of alloy powder CC, 150 g of nickel powder (>99% Ni; $d_{50}$=21 $\mu m$; 15wt. % with respect to the alloy powder used) and 25 g of ethylene bis-stearoylamide (2.13 wt. % with respect to the total metal content) whilst adding about 150 g of water. Pellets with a diameter of 4 mm and a thickness of 4 mm were compressed from this mixture. The shaped items were calcined for 2 h at 700° C. The average weight of one pellet was then 193.4 mg. The pellets were activated in 20% strength caustic soda solution for 2 h at 80° C. after calcination. The average thickness of the activated outer layer, determined using an optical microscope, was 0.2 mm. The oxygen absorption of the final catalyst, as a measure of the number of active nickel centers, was determined using TPO and was 1.04 mmol of $O_2$/g of catalyst.

EXAMPLE 1

A very free-flowing, pelletable catalyst mixture was; prepared from 1000 g of alloy powder A and 21.3 g of ethylene bis-stearoylamide (2.13 wt. % with respect to the total metal content). Activated pellets were prepared from this mixture in the same way as described for comparison example 1. The average weight of one pellet after calcination was only 157.3 mg. The average thickness of the activated outer layer was 0.47 mm for the same activation time. The oxygen absorption of the final catalyst was 2.16 mmol of $O_2$/g of catalyst.

EXAMPLE 2

A very free-flowing, pelletable catalyst mixture was prepared from 1000 g of alloy powder B and 21.3 g of ethylene bis-stearoylamide (2.13 wt. % with respect to the total metal content). Activated pellets were prepared from this mixture in the same way as described for comparison example 1. The average weight of one pellet after calcination was 185.8 mg. The average thickness of the activated outer layer was 0.65 mm for the same activation time.

Using the same granular fraction of alloy powder A, stable shaped items could not be obtained after activation, despite adding binder.

EXAMPLE 3

A very free-flowing, pelletable catalyst mixture was prepared from 1000 g of alloy powder C and 21.3 g of ethylene bis-stearoylamide (2.13 wt. % with respect to the total metal content). Activated pellets were prepared from this mixture in the same way as described for comparison example 1. The average weight of one pellet was only 152.1 mg. The average thickness of the activated outer layer was 0.3 mm for the same activation time.

COMPARISON EXAMPLE 2

A very free-flowing, pelletable catalyst mixture was prepared for a comparison catalyst in accordance with EP 0 648 534 A1 from 1000 g of alloy powder C, 150 g of nickel powder (>99% Ni; $d_{50}$=21 $\mu m$; 15 wt. % with respect to the alloy powder used) and 25 g of ethylene bis-stearoylamide (2.13 wt. % with respect to the total metal content). Activated pellets were prepared from this mixture in the same way as described for comparison example 1. The average weight of one pellet was 167.7 mg. The average thickness of the activated outer layer was 0.3 mm for the same activation time.

EXAMPLE 4

A very free-flowing, pelletable catalyst mixture was prepared from 1000 g of alloy powder D and 43 g of ethylene bis-stearoylamide (4.3 wt. % with respect to the total metal content). Activated pellets were prepared from this mixture in the same way as described for comparison example 1. The average weight of one pellet after calcination was only 168.9 mg. The average thickness of the activated outer layer was 0.3 mm for the same activation time.

No stable shaped items could be obtained after activation from an alloy powder with identical macroscopic composition, but with a specific interface density of less than 0.5 $\mu m^{-1}$, using the same amount of ethylene bis-stearoylamide.

EXAMPLE 5

A very free-flowing, pelletable catalyst mixture was prepared from 1000 g of alloy powder E and 43 g of ethylene bis-stearoylamide (4.3 wt. % with respect to the total metal content). Activated pellets were prepared from this mixture in the same way as described for comparison example 1. The average weight of one pellet after calcination was only 186.5 mg. The thickness of the activated outer layer was 0.35 mm for the same activation time.

APPLICATION EXAMPLE 1

The catalytic activity of catalysts from comparison examples 1 and 2 and from examples 1 to 3 were compared during the hydrogenation of nitrobenzene. For this purpose, 100 g of nitrobenzene and 100 g of ethanol were placed in a stirred autoclave with a capacity of 0.5 l, fitted with a gas stirrer. 10 g of the catalyst being investigated were suspended each time in the stirred autoclave using a catalyst basket so that the shaped catalyst material was thoroughly washed by the reactant/solvent mixture, and hydrogen was introduced. Hydrogenation was performed at a hydrogen pressure of 40 bar and a temperature of 150° C. The initiation temperature and the rate of hydrogen absorption were determined. The results are given in table 2. As a check, samples were withdrawn after 1, 2, 3, 4 and 5 h and analyzed using gas chromatography.

TABLE 2

Hydrogenation of benzene to aniline

| Example | Initiation temperature (° C.) | Rate of hydrogen absorption (1/h.g$_{cat}$) |
|---|---|---|
| CE 1 | 131 | 1.14 |
| E 1 | 115 | 1.59 |
| E 2 | 85 | 2.29 |
| E 3 | 112 | 2.12 |
| CE 2 | 118 | 1.88 |

The results in table 2 show that the catalysts E1 and E2 or E3 in accordance with the invention have a substantially increased activity for the hydrogenation of nitrobenzene to aniline as compared with the comparison catalysts CE 1 and CE 2. The low activity of the comparison catalysts can be attributed to the low concentration of activated metal due to the use of largely inert binder.

APPLICATION EXAMPLE 2

Acetone was hydrogenated to isopropanol in the trickle phase in a tubular reactor (d=25.4 mm, l=295 mm) using 25 ml of catalyst from comparison example 1 or example 1. Hydrogenation was performed initially at 5 bar hydrogen pressure, 70° C. and a LHSV of 0.2 h$^{-1}$. The LHSV was increased in 0.2 steps to 1.2 h$^{-1}$ over the course of the trial. The temperature increased to about 80° C. due to the exothermic reaction. After a period of 20 h, a sample of product was withdrawn and tested for conversion and isopropanol selectivity (table 3):

TABLE 3

Hydrogenation of acetone to isopropanol

| Example | Conversion (%) | Selectivity wrt isopropanol |
|---|---|---|
| CE 1 | 91.03 | 99.95 |
| E 1 | 99.41 | 99.99 |

The catalyst according to the invention had a significantly higher activity for comparable or slightly better selectivity under the same conditions of reaction.

In addition to application examples 1 and 2, the catalyst according to the invention is also suitable for the hydrogenation of nitro groups, the hydrogenation of imines, the hydrogenation of nitriles, the hydrogenation of CC double and CC triple bonds, the hydrogenation of carbonyl compounds, the hydrogenation of Co, Co$_2$ and their mixtures, the hydrogenation of sugars and the hydrogenation of aromatic rings.

At least one catalyst alloy with a phase structure incorporating small volumes and in which, on the basis of a quantitative metallographic test, the largest phase by volume has a specific interface density of greater than 0.5 µm$^{-1}$, and optionally containing one or more promoters, is obtainable by preparing a mixture of powders, wherein the catalyst alloys each contain a catalytically active catalyst metal and at least one extractable alloying component. A homogenized mixture is prepared by adding moistening agents and/or additives such as shaping aids, lubricants, plasticizers and/or pore producers and this is shaped to give the desired shaped items. The final catalyst is obtained after calcining the shaped item and activating the catalyst precursor obtained in this way by partial extraction of the extractable alloying component and after a final wash process.

Further variations and modifications of the foregoing will be apparent to those skilled in the art and are intended to be encompassed by the claims appended hereto.

German priority application 197 21 898.9 is relied on and incorporated herein by reference.

We claim:

1. A shaped, activated metal, fixed-bed catalyst with a pore volume of 0.05 to 1 ml/g and an outer activated layer consisting of a sintered, finely-divided, catalyst alloy and optionally promoters, wherein the catalyst alloy has metallurgical phase domains, in which the largest phase by volume has a specific interface density of more than 0.5 µm$^{-1}$, and wherein said catalyst is produced without any binders and is calcined only at a temperature below 850° C.

2. The shaped, activated metal, fixed-bed catalyst according to claim 1, wherein the catalyst alloy is an alloy of a catalyst metal selected from the group consisting of nickel, cobalt, copper, iron and mixtures thereof with an extractable alloying component selected from the group consisting of aluminum, zinc, silicon and mixtures thereof, wherein the catalyst metal and the extractable alloying component are present in a ratio by weight of 80:20 to 20:80.

3. The shaped, activated metal, fixed-bed catalyst according to claim 2, wherein the alloying component is a mixture of aluminum with zinc or silicon.

4. The activated metal, fixed-bed catalyst according to claim 1, further comprising at least one promoter selected from the group consisting of a transition metal from Groups 3B to 7B, Group 8, and Group 1B of the Periodic Table of Elements and the rare-earth metals in an amount of said promoter up to 20 wt. %, with respect to the total weight of catalyst.

5. A process for the hydrogenation of a nitro group, of an organic compound, comprising:

reacting said compound with hydrogen in the presence of the catalyst of claim 1.

6. A process for the hydrogenation of an imine compound comprising:

reacting said compound with hydrogen in the presence of the catalyst of claim 1.

7. A process for the hydrogenation of a nitride compound comprising:

reacting said compound with hydrogen in the presence of the catalyst of claim 1.

8. A process for the hydrogenation of an organic compound having a carbon to carbon double or triple bond comprising:

reacting said compound with hydrogen in the presence of the catalyst of claim 1.

9. A process for the hydrogenation of a carbonyl compound comprising:

reacting said compound with hydrogen in the presence of the catalyst of claim 1.

10. A process for the hydrogenation of an organic compound having at least one CO or $CO_2$ group comprising:

reacting said compound with hydrogen in the presence of the catalyst of claim 1.

11. A process for the hydrogenation of a sugar compound comprising:

reacting said compound with hydrogen in the presence of the catalyst of claim 1.

12. A process for the hydrogenation of a compound with aromatic rings comprising:

reacting said compound with hydrogen in the presence of the catalyst of claim 1.

13. The shaped, activated metal, fixed-bed catalyst according to claim 1, wherein the specific interface density is defined as:

$$Sv = \frac{4}{\pi} \cdot \frac{\text{Perimeter (phase)}}{\text{Area (phase)}}.$$

14. A method of making the shaped, activated metal, fixed-bed catalyst body according to claim 1 comprising:

forming a melt of a catalyst metal and aluminum, rapidly cooling said melt to a temperature of less than 700° C. in less than two minutes, to thereby produce a finely divided powder, optionally adding a promoter selected from the group consisting of a transition metal of Group 3B to 7B, Group 8, and Group 1B of the Periodic Table of Elements and the rare earth metals, adding at least one of a moistening agent, lubricant, plasticizer and pore former, to form a mixture homogenizing said mixture to obtain a shapable mixture, optionally extruding, pelleting or compacting, and shaping to obtain the shaped catalyst.

15. The method according to claim 14, wherein said metal alloy has an average particle size of 10 to 1000 microns.

16. The method according to claim 14, wherein said powder has a bulk density of 1 to 3 kg/l.

17. The method according to claim 14, wherein the extractable metal is aluminum, zinc or silicon.

18. The method according to claim 14, further comprising:

drying at a temperature of 80 to 120° C. and calcining at a temperature below 850° C.

19. The method according to claim 18, further comprising:

contacting the shaped catalyst body with a caustic soda solution to thereby extract said non-catalytic component of said alloy and forming a catalytically active outer layer on said body.

20. The shaped, activated metal, fixed-bed catalyst according to claim 1, wherein the catalyst is calcined only at a temperature between 200 and 700° C.

* * * * *